(12) United States Patent
Richardson et al.

(10) Patent No.: US 9,977,004 B2
(45) Date of Patent: May 22, 2018

(54) SYSTEMS AND METHODS FOR CONTROLLING CATIONIC WATER TREATMENT ADDITIVES

(71) Applicant: CHEMTREAT, INC., Glen Allen, VA (US)

(72) Inventors: John Richardson, Hanover, VA (US); Douglas McIlwaine, Ashland, VA (US); Benjamin Niemaseck, Chesterfield, VA (US)

(73) Assignee: CHEMTREAT, INC., Glen Allen, VA (US)

( * ) Notice: Subject to any disclaimer, the term of this patent is extended or adjusted under 35 U.S.C. 154(b) by 310 days.

(21) Appl. No.: 14/579,663

(22) Filed: Dec. 22, 2014

(65) Prior Publication Data

US 2015/0260702 A1   Sep. 17, 2015

Related U.S. Application Data

(60) Provisional application No. 61/952,846, filed on Mar. 13, 2014.

(51) Int. Cl.
| | |
|---|---|
| *G01N 33/18* | (2006.01) |
| *C02F 1/00* | (2006.01) |
| *C02F 1/50* | (2006.01) |
| *G01N 31/22* | (2006.01) |

(52) U.S. Cl.
CPC ......... *G01N 33/1813* (2013.01); *C02F 1/008* (2013.01); *C02F 1/50* (2013.01); *C02F 2209/005* (2013.01); *G01N 31/22* (2013.01)

(58) Field of Classification Search
CPC . A01N 51/00; Y10T 436/13; Y10T 137/0318; Y10T 436/12; Y10T 436/25125; B01J 2219/00576; B01L 3/5027; G01N 2021/6439; G01N 33/582; G01N 21/6428; G01N 2021/6417; G01N 2021/6421; G01N 2021/6432; G01N 33/1813; G01N 31/22; C02F 1/008; C02F 1/50; C02F 2209/005
See application file for complete search history.

(56) References Cited

U.S. PATENT DOCUMENTS

| | | | |
|---|---|---|---|
| 3,992,149 A | 11/1976 | Wang | |
| 5,702,684 A | 12/1997 | McCoy et al. | |
| 6,329,165 B1 * | 12/2001 | Chattoraj | C12Q 1/04 435/29 |

OTHER PUBLICATIONS

Buzády et al., "Determination of uranine tracer dye from underground water of Mecsek Hill, Hungary", J. Biochem. Biophys. Methods, 2006, v. 69, pp. 207-214.*
Sep. 13, 2016 International Preliminary Report on Patentability and Written Opinion issued in PCT/US2014/071960.
May 26, 2015 International Search Report and Written Opinion issued in PCT/US2014/071960.

(Continued)

*Primary Examiner* — Yelena G Gakh
(74) *Attorney, Agent, or Firm* — Oliff PLC

(57) ABSTRACT

Systems and methods are provided for measuring the amount of cationic organic water treatment additives in water systems. Disclosed systems and methods monitor, analyze and control the amounts of cationic organic water treatment additive supplied to the water. Disclosed systems and methods may include various dyes and surfactants for facilitating the monitoring and control of the cationic organic water treatment additives.

28 Claims, 11 Drawing Sheets

(56) References Cited

OTHER PUBLICATIONS

Perez-Ruiz et al., "Spectrofluorimetric determination of paraquat by manual and flow injection methods", The Analyst, vol. 123, No. 7, Jul. 1998, pp. 1577-1581.

Yao et al., "Determination of paraquat in water samples using a sensitive fluorescent probe titration method", Journal of Environmental Sciences, vol. 25., No. 6, Jun. 13, 2013, pp. 1245-1251.

\* cited by examiner

SYSTEMS AND METHODS FOR CONTROLLING CATIONIC WATER TREATMENT ADDITIVES

This application claims the benefit of U.S. Provisional Application 61/952,846, filed Mar. 13, 2014. The disclosure of the prior application is hereby incorporated by reference herein in its entirety.

TECHNICAL FIELD

This application is directed to systems and methods for analyzing cationic organic water treatment additives in water systems and treating the same. Cationic organic water treatment additives can include, for example, cationic biocides, cationic surfactants, and cationic polymers.

BACKGROUND

A number of cationic organic water treatment additives have been developed for various applications in industrial water systems. For example, cationic biocides, or quaternary amine compounds (quat) have been developed for use in water treatment for suppressing the growth of microorganisms including, for example, fungus, mold and bacteria. These compounds contain, for example, a protonated nitrogen or phosphorus atom bound to hydrophobic alkyl and aryl groups, and work like soaps or detergents in disrupting the osmotic equilibrium of living cells. Deactivating or otherwise neutralizing these cationic biocides or quat can be desirable prior to discharging the treated water via blowdown or other process.

Compounds, such as anionic surfactants, have been developed for deactivating or otherwise neutralizing the active or toxic form of quat ("free" quat) before the treated water is discharged. However, existing methods are severely limited in that there is no way to know whether the anionic surfactants are effective. This is because existing tests only measure total quat and not the free or active form. Thus, a test might show too much quat because it also picks up the inactive from in the system, regardless of whether the inactive form might still exist. In order to apply these treatments efficiently and/or monitor the effectiveness of a cationic biocide remediation program, a fast and accurate method for determining the concentration of the free quat residual in the water stream would be of particular benefit.

Few reliable methods currently exist for the detection and quantification of quat. For example, the Hach QAC Method (8337 Direct Binary Complex Method) uses two reagents and is very difficult to administer and is subject to inaccuracies resulting from, for example, noise from cloudy water. It also suffers from much interference that makes rapid and accurate measurements of quat residuals difficult. Moreover, existing methods often suffer from interference associated with common ions including, for example, calcium, chlorine, magnesium and iron. Other compounds that can interfere with detection and quantification of quat include compounds associated with common surfactants and treatment compounds such as, for example, sodium lauryl sulfate and sodium polyphosphate. A chart reflecting some of these known interferences is provided below in Table 1. These interferences limit the usefulness of such methods, particularly when the goal is to perform rapid and accurate measurements of quat.

| Interfering substance | Interference level |
| --- | --- |
| Calcium (as $CaCO_3$) | Positive interference above 1350 mg/L |
| Chlorine, HOCl and OCl− | Positive interference above 7 mg/L |
| Cyanuric acid | Negative interference above 70 mg/L |
| Igepal ™ nonionic surfactant | Positive interference above 3 mg/L |
| Iodine, $I_3$− | Positive interference above 3 mg/L |
| Iron, $Fe^{3+}$ | Positive interference above 80 mg/L |
| Liquimine ™ 14-P, filming amine | Positive interference above 1825 mg/L |
| Magnesium, $Mg^{2+}$ | Positive interference above 1350 mg/L |
| Niaproof ™ anionic surfactant | Negative interference above 11 mg/L |
| Polyacrylic acid | Negative interference above 16 mg/L |
| Sodium lauryl sulfate | Negative interference above 8 mg/L |
| Sodium polyphosphate | Positive interference above 1325 mg/L |
| Tribenzylamine | Positive interference above 7 mg/L |
| Triton X-100 ™ nonionic surfactant | Positive interference above 4 mg/L |
| Urea | Positive interference above 8 mg/L |
| Highly buffered samples or extreme sample pH | May exceed the buffering capacity of the reagents and require sample pretreatment. Adjust the sample pH between 3 and 5 by using a pH meter or pH paper and adding dropwise an appropriate amount of acid or base such as 1.0N Sulfuric Acid Standard Solution or 1.0N Sodium Hydroxide Standard Solution. If significant volumes of acid or base are used, a volume correction should be made. |

Another conventional method is high pressure liquid chromatography (HPLC). HPLC enables the dissection of complex mixtures into individual constituents. However HPLC measures total quaternary amine compound and is not able to measure only the amount of the quat that is free (unbound) in solution.

The ability to determine the concentration of the unbound free quat is desirable, as is the ability to distinguish between bound and free quat concentrations within a sample. Bound quat is that portion of the cationic quaternary amine compound that is strongly bound to a corresponding anionic compound and, therefore, exhibits significantly reduced antimicrobial activity compared to free quat present in the system. For example, the positively charged ammonium cation of the quat can be counter-balanced by a strong anion which renders the quat inactive. Existing methods only measure total quat and cannot distinguish between bound and free quat. Further, no automated on-line system currently exists for the detection, measurement and control of residual quat, or for the measurement and control of other cationic organic water treatment additives.

These and other issues are addressed by the present disclosure. It is an object of this disclosure to provide novel systems and methods for the fast and accurate quantification of the concentration of these cationic organic water treatment additives and, in particular, active forms of the additives within an aqueous stream as well as novel systems and methods for utilizing this improved quantification for detecting, measuring and controlling cationic organic water treatment additive residuals in industrial water systems.

One advantage of the present disclosure over existing methods for the measurement of, for example, cationic biocide residuals, such as the QAC and HPLC methods, is that these new systems and methods measure only the amount of free quat versus total quat. Accordingly, the present disclosure allows for the more accurate measurement of the amount of anti-microbially active cationic biocide present in an industrial water stream and can also quantify the amount of cationic surfactant and cationic polymer present in an industrial water stream.

SUMMARY

In a first embodiment, there is provided a method for analyzing water that includes a cationic organic water treatment additive. The method may include applying to the water a fluorescent first dye with an affinity for the cationic additive; applying to the water a fluorescent second dye with a relatively lesser affinity for the cationic additive than the first fluorescent dye; and then measuring a fluorescence parameter of the water.

In another embodiment, there is provided a method for analyzing water that includes a cationic organic water treatment additive. The method may include applying to the water an anionic dye with a relatively high affinity for an active form of the cationic additive and a relatively low affinity for an inactive form of the cationic additive; and then measuring a parameter of the water that is related to the amount of the active form of the cationic additive.

In another embodiment, there is provided a kit for analyzing water. The kit may include a dye infusion unit configured to apply to the water an anionic dye with a relatively high affinity for an active form of a cationic organic water treatment additive and a relatively low affinity for an inactive form of the cationic additive; a sensor for measuring a parameter of the water; and a control unit configured to analyze the parameter and determine the amount of the active form of the cationic additive in the water based on the parameter.

In another embodiment, there is provided a method for analyzing water that includes a cationic organic water treatment additive. The method may include adding to the water a first dye with an affinity for the cationic additive; adding to the water an anionic surfactant that can interfere with the affinity of the first dye for the cationic additive; and measuring a parameter of the water.

In another embodiment, there is provided a method for treatment of a water stream that includes a cationic organic water treatment additive in a water system. The method may include adding to the water a first fluorescent dye with an affinity for the cationic additive; adding to the water a second fluorescent dye with a relatively lesser affinity for the cationic additive than the first fluorescent dye; measuring a parameter of the water; applying to the water an anionic surfactant that can interfere with the affinity of the first fluorescent dye for the cationic additive; and controlling the amount of anionic surfactant added to the water based on the measured parameter.

In another embodiment, there is provided a system for treatment of a water stream including a cationic organic water treatment additive in a water system. The system may include an infusion device configured to apply an amount of an active form of the cationic additive to the water stream; a measurement device configured to measure an amount of the cationic additive in the water stream; a monitor configured to monitor an output from the measurement device; and a controller configured to adjust the amount of the active form of the cationic additive applied to the water stream based on the amount of the cationic additive in the water stream.

In another embodiment, there is provided a method for analyzing water that includes a cationic organic water treatment additive. The method may include applying to the water a first dye with an affinity for the cationic additive; applying to the water a second dye with a relatively lesser affinity for the cationic additive than the first dye; and measuring a parameter of the water.

DETAILED DESCRIPTION

Figure 1:
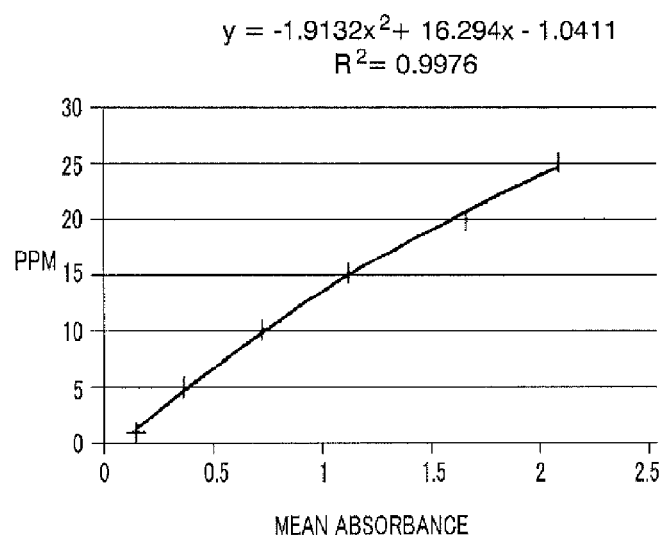
FIG. 1 is a graph illustrating a standard curve for average absorbance data using Eosin and ADBAC samples.

The inventors have discovered that the effectiveness of a cationic organic water treatment additive can depend on and be proportional to the existence and amount of active form of the additive present. For purposes of this disclosure, the active form of an additive is defined as having a cationic portion that has a free positive charge. The inventors have further discovered novel methods and systems for the identification, quantification and control of the active form of the cationic organic water treatment additive in water systems. While it is known in the art to identify free or active forms of halogens, identification, quantification and control of free quaternary amine compound, for example, is not presently known or contemplated. The inventors have discovered a test for tagging the active foal' of the cationic organic water treatment additive, such as free quat, which results in the unexpectedly effective approach for identification and quantification of the active form of the cationic organic water treatment additive.

Systems and methods of a first embodiment involve analyzing a water stream including a cationic organic water treatment additive in a water system by applying an anionic dye with a relatively high affinity (a propensity to chemically bind) for an active form of the cationic organic water treatment additive to a sample of the water stream, measuring an optical property of the sample (e.g., absorbance) and determining the amount of the active form of the cationic organic water treatment additive in the sample based on the absorbance of the sample. These methods provide an advantage over existing methods in that, among other things, the surfactants and other compounds and ions that are known to interfere with the existing methods do not interfere with the methods described herein.

In embodiments, the cationic organic water treatment additives include but are not limited to cationic surfactants, cationic polymers and cationic biocides. Examples of such surfactants include, but are not limited to, cationic quaternary and phosphonium surfactants such as trimethyl alkyl ammonium chlorides, benzalkonium chlorides and bromides, alkyl pryridinium ions and mixtures thereof. These surfactants are commonly used as cleaners and process additives in water treatment and textile applications, and as paper processing aids. Examples of such cationic polymers include, but are not limited to, those derived from high density charged monomers, poly-DADMAC, and polyamines derived from the reaction of dimethylamine with epichlorohydrin and mixtures thereof. Cationic polymers can be used as process additives in water treatment applications, most commonly as flocculants. The biocide may be, for example, a quaternary amine compound. In preferred embodiments, the cationic biocide may be alkyldimethylbenzyl ammonium chloride (ADBAC). The active from of the cationic biocide (the free quat) is a microbially active form. Other suitable biocides include, but are not limited to, Octyl Decyl Dimethyl Ammonium Chloride, Didecyl Dimethyl Ammonium Chloride, Dioctyl Dimethyl Ammonium Chloride, n-Alkyl dimethyl ethyl benzyl ammonium chloride, Tributyl tetradecyl phosphonium chloride and mixtures thereof.

The anionic dye may be any suitable dye for emitting or affecting an optical signal. For example, the dye may be an absorbent dye, a fluorescent dye or a phosphorescent dye. In preferred embodiments, the dye is a fluorescent anionic aromatic dye. These dyes bind to the active form of the cationic organic water treatment additive but will not bind to the inactive form. This is perhaps due to a common benzyl ring in the chemical structures of the dye and the active form of certain cationic organic water treatment additives. The anionic dye may be, for example, a polycyclic halogenated aromatic dye including, for example, Eosin B or Eosin Y, shown below.

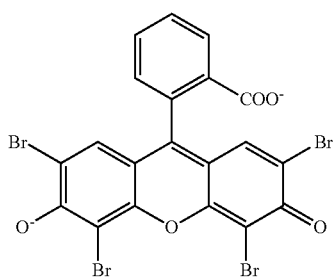

Eosin Y

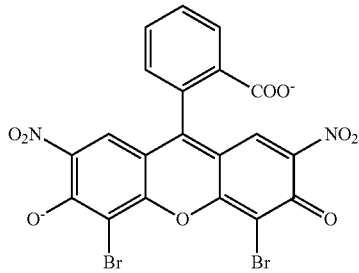

Eosin B

In the case of cationic biocides, the polycyclic halogenated aromatic dye forms a complex with the free quaternary amine compound. The resulting complex can have a different color (e.g., a pinkish color in solution) from the color of the unbound dye and absorbs light differently than the unbound dye.

Other suitable dyes may be selected from a group including, for example, 1,3,6,8-pyrenetetrasulfonic acid tetrasodium salt; 3,6-acridinediamine, N,N,N',N'-tetramethyl-monohydrochloride; 2-anthracenesulfonic acid sodium salt; 1,5-anthracenedisulfonic acid; 2,6-anthracenedisulfonic acid; 1,8-anthracenedisulfonic acid; anthra[9,1,2-cde]benzo[rst]pentaphene-5,10-diol, 16,17-dimethoxy-bis(hydrogen sulfate), disodium salt; bathophenanthrolinedisulfonic acid disodium salt; amino 2,5-benzene disulfonic acid; 4-aminophenyl-6-methylbenzothiazole; 1H-benz[de]isoquinoline-5-sulfonic acid, 6-amino-2,3-dihydro-2-(4-methylphenyl)-1,3-dioxo-, monosodium salt; phenoxazin-5-ium, 1-(aminocarbonyl)-7-(diethylamino)-3,4-dihydroxy-, chloride; benzo[a]phenoxazin-7-ium, 5,9-diamino-, acetate; 4-dibenzofuransulfonic acid; 3-dibenzofuransulfonic acid; 1-ethylquinaldinium iodide; fluorescein; fluorescein, sodium salt; benzenesulfonic acid, 2,2'-(1,2-ethenediyl)bis[5-[[4-[bis(2-hydroxyethyl)amino]-6-[(4-sulfophenyl)amino]1,3,5-triazin-2-yl]amino]-tetrasodium salt; C.I. Florescent Brightener 230; benzenesulfonic acid, 2,2'-(1,2-ethenediyl)bis[5-[[4-[bis(2-hydroxyethyl)amino]-6-[(4-sulfophenyl)amino-1,3,5-triazin-2-yl]amino]-, tetasodium salt; 9,9'-biacridinium, 10,10'-dimethyl-, dinitrate; 1-deoxy-1-(3,4-dihydro-7,8-dimethyl-2,4-dioxobenzo[g]pteridin-10(2H)-yl)-ribitol; mono-, di-, or tri-sulfonated napthalenes selected from the group consisting of 1,5-naphthalenedisulfonic acid, disodium salt (hydrate); 2-amino-1-naphthalenesulfonic acid; 5-amino-2-naphthalenesulfonic acid; 4-amino-3-hydroxy-1-naphthalenesulfonic acid; 6-amino-4-hydroxy-2-naphthalenesulfonic acid; 7-amino-1,3-naphthalenesulfonic acid, potassium salt; 4-amino-5-hydroxy-2,7-naphthalenedisulfonic acid; 5-dimethylamino-1-naphthalenesulfonic acid; 1-amino-4-naphthalene sulfonic acid; 1-amino-7-naphthalene sulfonic acid; and 2,6-naphthalenedicarboxylic acid, dipotassium salt; 3,4,9,10-perylenetetracarboxylic acid; benzenesulfonic acid, 2,2'-(1,2-ethenediyl)bis[5-(4-phenyl-2H-1,2,3-triazol-2-yl)-, dipotassium salt; benzenesulfonic acid, 5-(2H-naphtho[1,2-d]triazol-2-yl)-2(2-phenylethenyl)-sodium salt; pyranine; quinoline; 3H-phenoxazin-3-one, 7-hydroxy-, 10-oxide; xanthylium, 9-(2,4-dicarboxyphenyl)-3,6-bis(diethylamino)-chloride, disodium salt; *phenazinium*, 3,7-diamino-2,8-dimethyl-5-phenylchloride; benzenesulfonic acid, 2,2'-(1,2-ethenediyl)bis[5-[[4-[bis(2-hydroxyethyl)amino]-6-[(4-sulfophen-yl)amino]-1,3,5-triazin-2-yl]amino]-, tetrasodium salt; benzenesulfonic acid, 2,2'-(1,2-ethenediyl)bis[5-[[4-[(2-hydroxypropyl)amino]-6-(phenylam-ino)-1,3,5-triazin-2-yl]

amino]-, disodium salt; xanthylium, 3,6-bis(diethylamino)-9-(2,4-disulfophenyl)-, inner salt, sodium salt; benzenesulfonic acid, 2,2'-(1,2-ethenediyl)bis[5-[[4-[(aminomethyl)(2-hydroxyethyl)amino]-6-(ph-enylamino)-1,3,5-triazin-2-yl]amino]-, disodium salt; benzenesulfonic acid, 2,2'-([1,1'-biphenyl]-4,4'-diyldi-2,1-ethenediyl)bis, disodium salt; benzenesulfonic acid, 5-(2H-naphtho[1,2-d]triazol-2-yl)-2-(2-phenylethenyl), sodium salt; 7-benzothiazolesulfonic acid, 2,2'-(1-triazene-1,3-diyldi-4,1-phenylene)bis[6-methyl-disodium salt; and all ammonium, potassium and sodium salts thereof; and all mixtures thereof.

Measuring a light absorbance of a sample of a water stream and determining the amount of the active form of the cationic organic water treatment additive in the sample based on the light absorbance of the sample can include the following steps, which for illustrative purposes, are described in the context of a cationic biocide. Mixing a small quantity of a dye with a solution containing the cationic biocide then measuring the intensity of the color (absorbance) at a suitable wavelength of, for example, 550 nm, at which the intensity of the color at about 550 nm is proportional to the concentration of the free cationic biocide present in the solution. The dye may be mixed at from about 0.01 to 0.5 grams, or more preferably, 0.03 to 0.1 grams of a dilute (0.5%) solution. The cationic biocide in solution may be at concentration of from about 0.5 to 200 mg/L, or more preferably, 1 to 100 mg/L. Absorbance may be measured using any suitable colorimeter known in the art such as, for example, a Hach PCII 550 nm colorimeter. Because the dye interacts (binds) with the free quat, the dye-bound free quat absorbs color at 550 nm wavelength differently than the dye itself, disclosed methods and systems are able to detect the amount of free quat in the sample. Disclosed methods and systems are not limited to absorbing color at 550 nm. As will be understood by one of ordinary skill in the art, other suitable wavelengths are acceptable and depend, in part, on the dye and the quat. In this manner, toxic or active quat is differentiated from total or bound quat.

The Standard Curve

In embodiments, the method may further comprise comparing the absorbance of the sample to the standard absorbance curve for the dye and the active form of the cationic organic water treatment additive. Using a series of samples of known concentrations, a standard curve such as shown in FIG. 1 can then be generated by maintaining a constant concentration of the dye while varying the concentration of the active form of the cationic organic water treatment additive.

In preferred embodiments, an exemplary standard curve is generated using Eosin Y and a cationic biocide, ADBAC. The Eosin dye was prepared by dissolving 0.5 grams of Eosin Y in 100 grams of ethylene glycol. In order to generate a standard curve, standard solutions of ADBAC were prepared by diluting a 50% solution of the quat to final concentrations of 1, 5, 10, 15, 20 and 25 ppm as active quat in Ashland, Va. tap water. Two drops of the dye solution were added to each of the standard 10 ml samples of the quat, and the absorbance of the resulting colored solution was then measured using a Hach PCII 550 nm colorimeter using a sample cell path length of 2.54 cm (1 inch). Each sample was prepared and run in triplicate. The average absorbance data for each of the samples is reported below in Table 2 and the corresponding standard curve that was generated from these results is shown in FIG. 1.

| Concentration (ppm) | Average Absorbance |
|---|---|
| 1 | 0.149 |
| 5 | 0.371 |
| 10 | 0.723 |
| 15 | 1.12 |
| 20 | 1.662 |
| 25 | 2.085 |

In embodiments, in order to measure the active form of the cationic organic water treatment additive in an aqueous stream accurately, the water is preferably relatively clear and free of particulates. Accordingly, for many aqueous systems, the disclosed systems and methods may further comprise filtering the sample of the water stream using vacuum filtration before measuring the absorbance of the sample. The sample may first be filtered or otherwise prepared to remove substantially all particulates and reduce turbidity to provide samples suitable for colorimetric analysis. This preparation may be accomplished using a vacuum filtration process employing a series of filters of decreasing pore size filter in a series of filtration steps, such as, for example, from 25 to 1.5 µm. The final filtration may, for example, be performed using a 1.5 µm filter. An exemplary filtration process useful in connection with the disclosed systems and methods is detailed next.

Filtering the water may include preparing a suitable filtration apparatus such as, for example, a vacuum pump attached to a Buchner flask fitted with a Buchner funnel. For example, 100 ml of waste water is filtered through a Whatman Filter Paper grade 4, pore size >20-25 µm for the initial filtration. This filtrate is then passed to the next filtration step. In this step, the water is filtered using Whatman Filter Paper grade 2, pore size >8 µm for the second filtration. In the next step, the water from the previous filtration step is filtered using Whatman Filter Paper grade 5, pore size >2.5 µm for the third filtration. This filtrate is then filtered a final time. An exemplary measurement process useful in connection with the disclosed systems and methods is detailed next.

A 10 ml syringe is filled with the filtrate from the previous filtration step, a 1.5 µm syringe filter is placed onto the end of the syringe, and the solution is dispensed through the filter into a sample vial. At this point, the water should be clear enough to allow for the measurement of the quat and exhibit, for example, a nephelometric turbidity unit (NTU) value of preferably less than 50, more preferably less than 25 and most preferably less than 5. The NTU measures how much light is scattered by suspended particles in the water. The greater the scattering, the higher the turbidity. Therefore, low NTU values indicate high water clarity, while high NTU values indicate low water clarity.

In order to measure the amount of the cationic organic water treatment additive in the filtered water, a sample of the filtered water is placed in the colorimeter sample cell. The colorimeter is zeroed using the sample of the filtered water. After zeroing the instrument on the filtered water sample, a second sample of the filtered water is prepared and 2 drops of the dye solution are added. The mixture of the filtered water and the dye is agitated through known means in the art to allow any bubbles generated during the agitation to dissipate. The mixed sample is placed in the colorimeter and the absorbance of the sample is read. The concentration of the active form of the cationic organic water treatment additive in the sample is determined by correlating the absorbance value read from the mixed sample with the standard curve generated for the particular dye solution.

Figure 11:
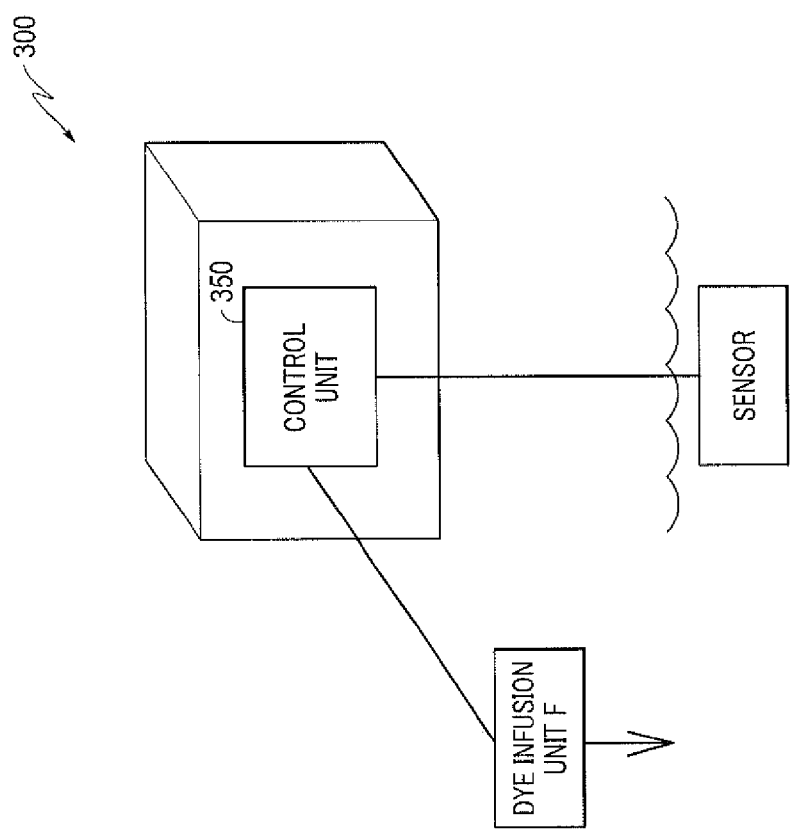
FIG. 11 is a schematic diagram of a kit for analyzing water according to an embodiment.

The above-described methods and systems may comprise a kit 300 or box suitable for effective transport of the disclosed tests from location to location according to another embodiment shown in FIG. 11. This permits easy application of the disclosed methods and systems at various sites such as, for example, water treatment sites. The kit may comprise a dye infusion unit F configured to applying to the water an anionic dye with a relatively high affinity for the active form of the cationic organic water treatment additive and a relatively low affinity for an inactive form of the cationic organic water treatment additive. The kit may also comprise a sensor 310 for measuring a parameter of the water and a control unit 350 configured to analyze the parameter and determine the amount of the cationic biocide in the water based on the parameter.

The kit may contain a Hach 550 nm colorimeter, and a dropper bottle full of the Eosin Y dye. Filtration of the water may be done separately. The absorbance of the solution that contains the dye and the active form of the cationic organic water treatment additive is read on the colorimeter, and that absorbance is the compared to conversion table to provide the amount of cationic organic water treatment additive in the water. The kit may analyze samples of water on the order of from about 1 to 100 mL, or more preferably, about 10 mL of water.

Disclosed systems and methods of another embodiment further relate to identification of the active form of the cationic organic water treatment additive. Conventional cationic organic water treatment additive measurement methods have drawbacks in the context of, for example, the food industry where, in the case of cationic biocides, quat-based disinfectants that are used to sanitize work space and equipment ultimately kill microbes downstream in waste treatment plants. In waste treatment plants, microbes are desirable for treating the water and occasionally are used for producing methane for fuel. Excess concentrations of active cationic biocides can disrupt the functioning of beneficial microbes present in the waste water treatment system and adversely affect the normal functioning of the system and raise environmental discharge issues. Anionic surfactants are used to neutralize the quat in the system and render the active quat inactive so that microbial activity is preserved in the waste treatment plant. Because conventional quat measurement methods are unable to determine the amount of active quat in the system, the application of anionic surfactants, or quat-neutralizers, cannot be effectively controlled.

In another embodiment, the addition of a fluorescent dye allows for the measurement of various compounds in water systems because it emits fluorescence. The dye may be any suitable polycyclic aromatic anionic water soluble molecule that possesses fluorescent properties. In preferred embodiments, the dye may be, for example, pyrenetetrasulfonic acid (PTSA) dyes. PTSA binds with the active form of the cationic organic water treatment additive such that the addition of the active form of the cationic organic water treatment additive to a constant volume water sample reduces the overall fluorescence signal of the sample because quat binds with PTSA and removes the fluorescent compound from the sample. The inventors discovered that, unexpectedly, the addition of certain anionic neutralizing compounds that neutralize the active form of the cationic organic water treatment additive can restore the fluorescence of such a sample.

Disclosed systems and methods of another embodiment relate to recovery of a fluorescent signal through the application of anionic surfactants such as, for example, an amphiphilic surfactant that may or may not be ethoxylated, which may contain a hydrophobic tail of carbon atoms attached to an anionic sulfate group. This embodiment may include applying a fluorescent dye with an affinity for the active form of the cationic organic water treatment additive to a sample of the water stream, applying an anionic surfactant for interfering with the affinity of the fluorescent dye for the active form of the cationic organic water treatment additive, measuring a fluorescent signal of the sample and determining the amount of the active form of the cationic organic water treatment additive in the sample based on the fluorescent signal of the sample. In preferred embodiments, determining the content of quat in an aqueous stream utilizes the application of an anionic surfactant such as, for example, a compound containing sodium laureth sulfate for interfering with the affinity of the fluorescent dye for the active form of the cationic organic water treatment additive and affecting the fluorescence emitted by the fluorescent dye. It is believed that this combination and subsequent reaction or complexing that occurs between the active form of the cationic organic water treatment additive and an anionic fluorescent dye molecule in solution reduces the strength of the fluorescence signal associated with the fluorescent molecule in the overall sample. Unexpectedly, the addition of certain anionic surfactants can reverse this binding/complexing effect because the surfactant competes with the fluorescent dye for the active form of the cationic organic water treatment additive, and can allow substantial recovery of the initial fluorescence signal.

A drop in fluorescence can be proportional to an increase in the concentration of the active form of the cationic organic water treatment additive in the system. This data can be used to control the anionic surfactant addition so that the surfactant is added until fluorescence is brought back up to a threshold level, which is inversely proportional to the amount of the active form of the cationic organic water treatment additive.

By monitoring the recovery of the fluorescence signal associated with the fluorescent chemicals in response to the controlled addition of suitable anionic surfactants, the residual concentration of the active form of the cationic organic water treatment additive can be determined with improved accuracy. Once the concentration of the active form of the cationic organic water treatment additive has been determined, the feed rate and/or mediating treatments can be controlled more precisely, thereby improving the overall performance of the monitored water system.

Also, as a result, by controlling the addition of an appropriate anionic surfactant to a water stream containing fluorescent molecules that have reacted with the active form of the cationic organic water treatment additive, it is possible to judge and control the concentration of the active form of the cationic organic water treatment additive with improved accuracy. This information regarding concentration of the residual, i.e., unreacted forms of the cationic organic water treatment additive can, in turn, be used for improving the control of cationic organic water treatment additives in aqueous systems such as the waste water systems in food plants, the discharge of a surface water system, a waste treatment plant or any industrial water system where the cationic nature of the cationic organic water treatment additive could impact the proper functioning of other system additives such as scale inhibitors. The information regarding concentration of unreacted cationic additive can also be used to control the amount of cationic organic water treatment additive when there is a system demand for the additive, e.g., to ensure that there is a sufficient quantity of cationic additive in the system.

In addition, information regarding the residual concentration of the cationic organic water treatment additives, can, in turn, be used for improving the control of the concentrations and performance of the cationic organic water treatment additive in aqueous system. This measurement also ensures that excess residuals of cationic surfactants and polymers can be controlled so that they do not adversely impact the performance of downstream filtration media and reverse osmosis equipment, and will not impact environmental toxicity profiles for potable or industrial effluent waters.

Example 1

A sample of PTSA was prepared to provide a 200 ppb concentration in tap water and its fluorescence signal measured using a fluorimeter. A cationic biocide composition or quat was then added to the sample in 2 ppm increments until the fluorescence stopped decreasing with added quat. A total of 18 ppm of quat was added before the fluorescence level reached a stable minimum. The decrease in fluorescence with increasing concentrations of quat is shown graphically in FIG. 2.

Figure 3:
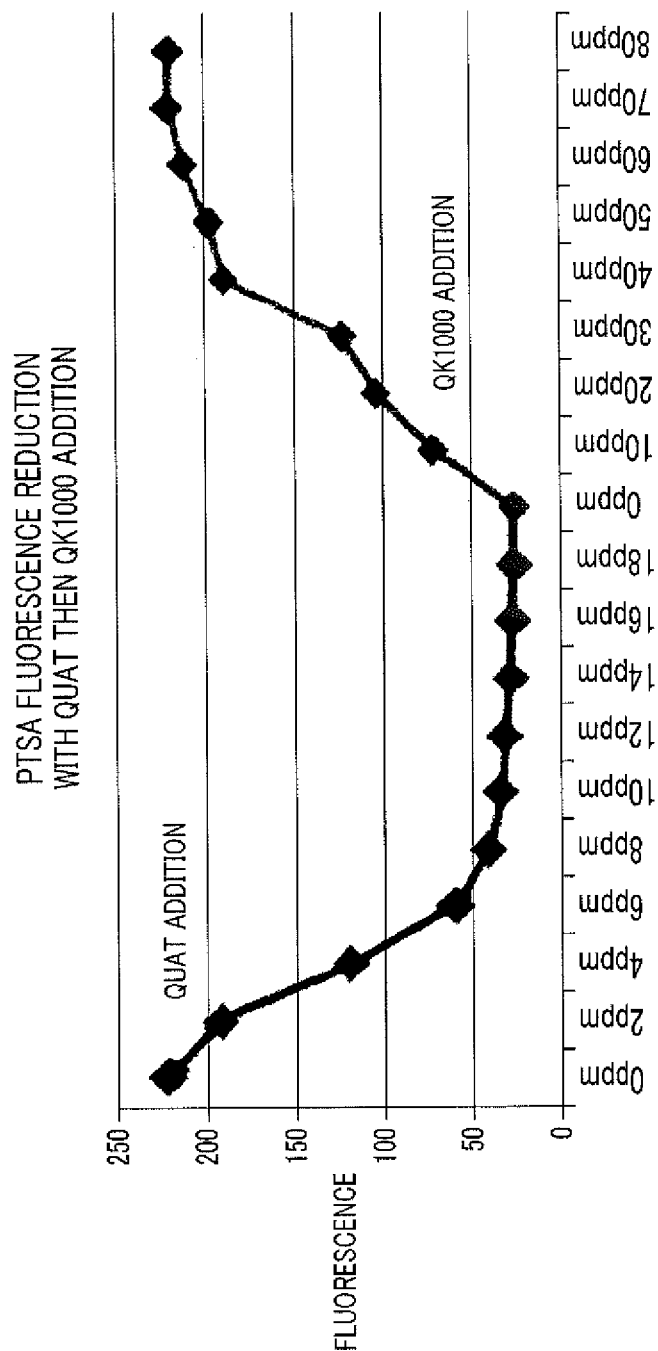
FIG. 3 is a graph illustrating PTSA fluorescence versus quat addition with an anionic surfactant according to an embodiment.

A solution of a biodegradable anionic surfactant, in this instance QK-1000 (sodium laureth sulfate) was then added to the solution in 10 ppm increments to determine if and to what degree, the addition of the surfactant would allow the PTSA fluorescence signal to recover after being suppressed by the addition of the quat. The surfactant was added up to a total concentration of 80 ppm which resulted in the fluorescence signal rebounding to approximately the same intensity as had been observed in the pretreatment sample. Both the initial decrease in fluorescence associated with the increasing quat concentration and the subsequently increasing fluorescence corresponding to the increasing concentrations of anionic surfactant is shown graphically in FIG. 3.

Although other disclosed embodiments are useful for evaluating samples drawn from an aqueous system and determining the level of the active form of the cationic organic water treatment additive in the system or sample, the accuracy of some of these methods depends to an extent on knowing with some degree of accuracy the concentration of the added dye in the monitored stream or sample. This can be a challenge for certain in-line evaluations, particularly in those instances in which the aqueous stream under evaluation represents the combination of several diverse streams, the concentration of the components of the stream are highly variable, the stream is particularly turbid, or there are other factors or components which would tend to interfere with the absorbance or fluorescence measurements. For instance, fluorescence, such as PTSA fluorescence, is sensitive to water volume. Thus, while some embodiments may comprise highly useful indicators of the active form of the cationic organic water treatment additives in a controlled sample or low-variable system setting, they may not be as accurate in water systems that involve real-time variable flow such that the overall volume of the system fluctuates. The inventors have discovered a further solution to this problem, as discussed next with respect to another embodiment.

Figure 2:
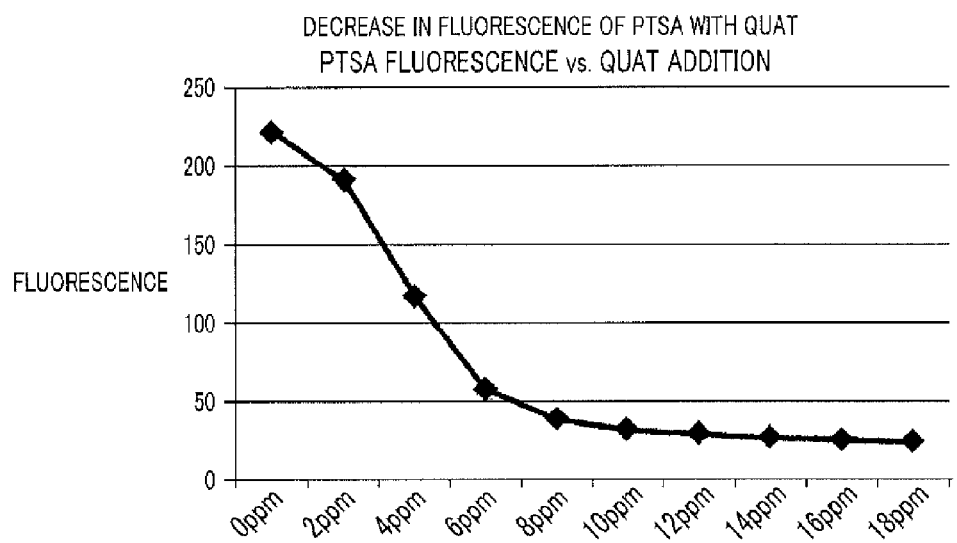
FIG. 2 is a graph illustrating PTSA fluorescence versus quat addition according to an embodiment.

The fluorescence chart for PTSA shown in FIG. 2 assumes a constant water volume sample. For example, the application of the active form of the cationic organic water treatment additive indication in some embodiments may be skewed if the volume of the water sample changed (e.g., if a constant amount of the cationic organic water treatment additive is added but the water stream volume is varied). The inventors have discovered that relating a first fluorescence indication to a second fluorescence indication establishes a ratio that is volume agnostic and can thus be used to monitor and control the application of the active form of the cationic organic water treatment additive to a real-time active water system.

This embodiment may include applying a first fluorescent dye with an affinity for the cationic organic water treatment additive to a sample of the water stream, applying a second fluorescent dye with a lesser affinity for the cationic organic water treatment additive to the sample of the water stream, applying an anionic surfactant for interfering with the affinity of the first fluorescent dye for the active form of the cationic organic water treatment additive (this step is described in connection with previous embodiments), and measuring a fluorescent signal of the first fluorescent dye and the second fluorescent dye to generate a ratio of the signal from the first fluorescent dye to the signal from the second fluorescent dye, determining the amount of the active form of the cationic organic water treatment additive in the sample based on the ratio, and controlling either the application of the anionic surfactant or the addition of cationic additive based on the measured ratio.

In this embodiment, the determining step may further comprise determining the amount of the active form of the cationic organic water treatment additive in the sample based on a ratio that is representative of the first and second fluorescence signals of the sample. This embodiment applies a two-dye system in which the dyes are introduced into the system in a known concentration ratio. The two dyes are selected to provide different measurable responses to the presence of the active forms of the cationic organic water treatment additives and anionic surfactants present within the monitored aqueous stream. Subsequent measurement of the relative expression of the two dyes in the monitored aqueous stream can then be used to calculate a ratio that is less subject to some of the measurement variability concerns associated with the single dye methods. The two-dye method can also provide a more complete analysis of the relative concentrations of active cationic organic water treatment additive residuals and anionic surfactants within the stream.

In this embodiment, the first dye substantially interacts with the active form of the cationic organic water treatment additive, e.g. by associating with the active additive compound through ionic or other intermolecular forces. The second dye substantially does not interact with the active form of the cationic organic water treatment additive, and is preferably inert with respect to the active cationic additive. For example, the first dye may be a fluorescent dye according to the previous embodiments, such as PTSA. The second dye may be a dye with a fluorescent signal that, unlike the fluorescent signal associated with first dye, is not significantly impacted by the addition of the cationic organic water treatment additive to the solution such as, for example, a fluorescent substance with a weak anionic character. In preferred embodiments, the dye may be uranine. Uranine is a non-reactive dye. The fluorescence of uranine is not affected by the amount of cationic organic water treatment additive in the solution. This phenomenon is illustrated in Example 2 with respect to a cationic biocide.

Example 2

The fluorescence signal of dilute uranine solutions was examined at various wavelengths from about 500 nm to about 545 nm using a first solution that was free of quat and a second solution that also included 10 ppm of an ADBAC quat. These results are shown in FIG. 4.

Figure 4A:
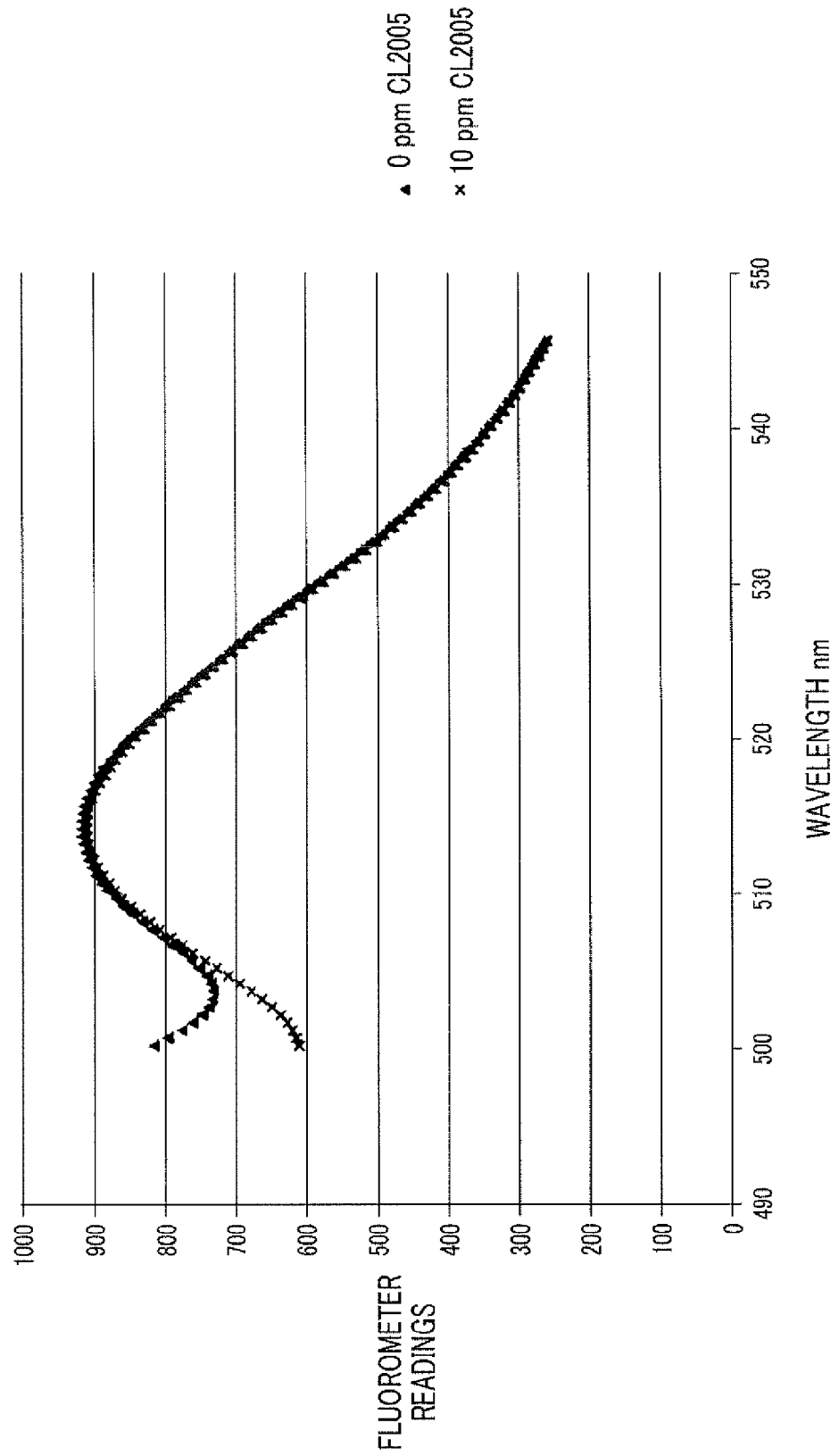
FIG. 4A is a graph illustrating the fluorescence signal of uranine examined at various wavelengths according to an embodiment.

As shown in FIG. 4A, the fluorescence signal of uranine (non-reactive dye) is not significantly impacted by the presence of quat in the solution, whereas the PTSA (a reactive dye) fluorescence signal is reduced by increasing concentrations of quat. This differential response between the combination of relatively reactive and relatively non-reactive dyes to the presence of the quat provides another improved method for determining the concentration of the active quat in an aqueous stream.

When the non-reactive dye is added to a water stream, it will produce a separate and distinct corresponding optical signal that, together with the signal of the reactive dye, will define a baseline optical signal ratio. When both a reactive and non-reactive dye are added to an aqueous stream or sample that includes a concentration of one or more cationic organic water treatment additive molecules, the optical signal associated with the reactive dye will decrease if the flow of water containing more of the active form of the cationic organic water treatment additive through the system is increased, because the fluorescent molecule binds with the active form of the cationic organic water treatment additive effectively reducing the concentration of the fluorescent dye. In contrast, the fluorescence signal associated with the non-reactive dye remains unchanged because the concentration of the non-reactive dye remains substantially unchanged. The decrease in the signal associated with the reactive dye will also alter the fluorescence signal ratio, which corresponds to the concentration of the cationic organic water treatment additive in the sample.

As described throughout this disclosure, the amount of the active form of the cationic organic water treatment additive in an aqueous system can be reduced by adding an appropriate anionic surfactant to a system where it will react with and remove cationic organic water treatment additive from solution. When an appropriate anionic surfactant is added to a system including a combination of the first fluorescent dye (reactive) and the second fluorescent dye (non-reactive), a corresponding increase in the signal associated with the reactive dye will be observed. As a result, the quantity of anionic surfactant necessary to remove substantially all of the targeted active form of the cationic organic water treatment additive may be adjusted to maintain a fluorescence signal ratio close to the baseline fluorescence signal ratio. This recovery of the signals to a level associated with the original ratio will indicate that the system does not include any substantial quantity of the active form of the cationic organic water treatment additive. Unlike the PTSA signal alone, the ratio signal will not be substantially affected by water volume and is therefore useful in real-time applications. Monitoring and controlling the neutralization of the active form of the cationic organic water treatment additive in this manner avoids the need for preventive overdosing of the anionic surfactant and the associated expenses.

Also, if there is a demand for the cationic additive in a water system, the amount of cationic additive can be adjusted to maintain the fluorescence signal above a certain level to ensure that there is a sufficient amount of active cationic additive.

For water systems that have a demand for the cationic additive, the system demand can also be determined by adding a known amount of cationic additive to the water system and measuring the response of the signal of the reactive dye, or measuring the response of the ratio of the reactive dye signal and non-reactive dye the non-reactive dye signal, and comparing the response to an expected response that is based, for example, on a premeasured standard curve. By way of illustration, a standard curve showing an expected response in a water sample having no demand for cationic additive can be generated by measuring the response of the ratio of the reactive dye signal and non-reactive dye signal when known amounts of cationic additives are added to the water. This standard curve can be used to determine the demand for the cationic additive in a water system by adding a known amount of cationic additive to the system until the measured response corresponds to the response expected from the standard curve, i.e., the expected change in the fluorescence parameter will be seen once sufficient cationic additive has been added to the water system to meet the demand. This information can be used to monitor the system demand and to control the amount of cationic additive that is added to the system to ensure that the demand is met.

Figure 4B:
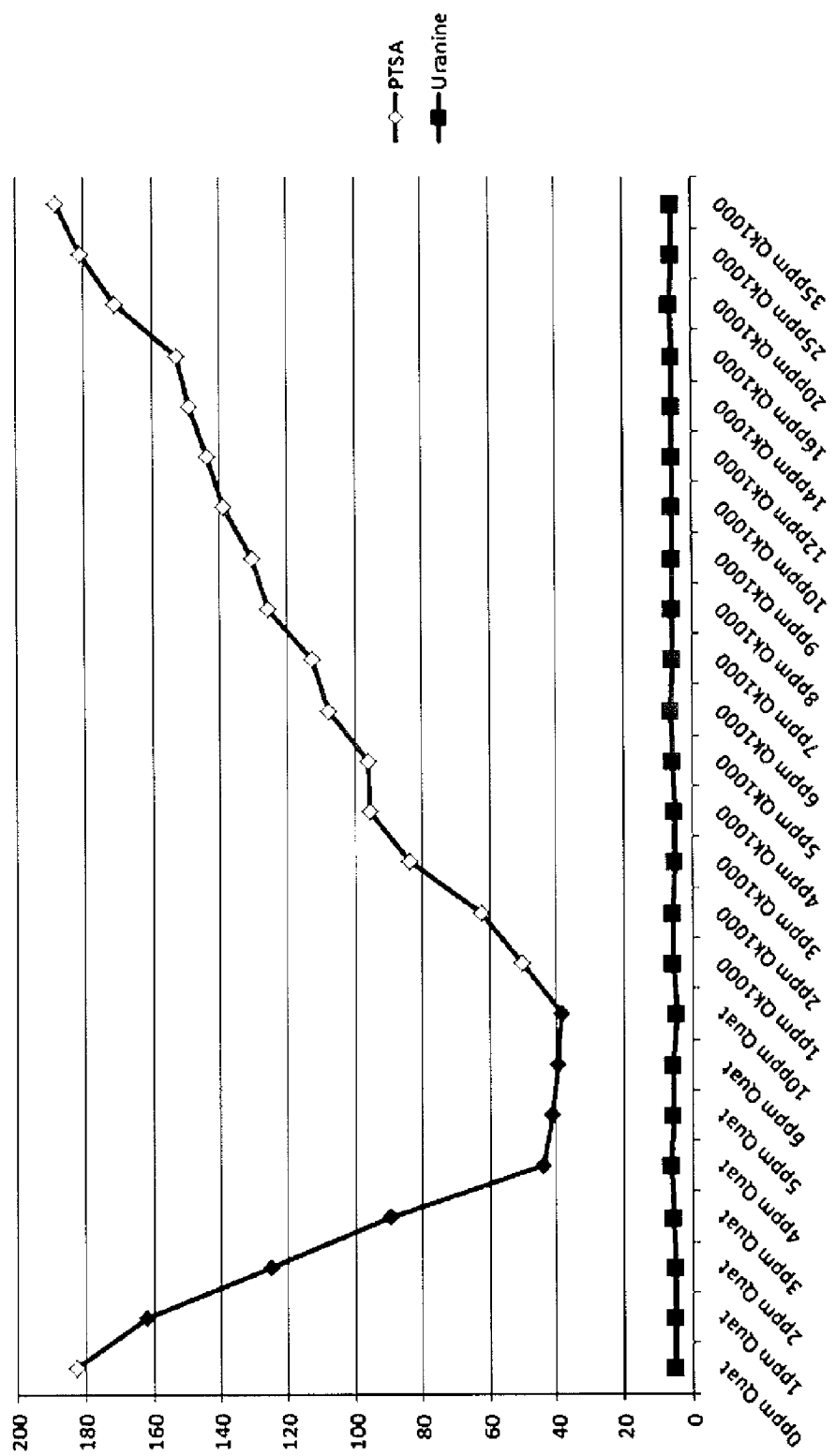
FIG. 4B is a graph illustrating the fluorescence signal of PTSA relative to uranine at various concentrations of biocide and anionic surfactant according to an embodiment.

FIG. 4B illustrates an example of the phenomenon described above. FIG. 4B shows the fluorescence signal of PTSA relative to the fluorescence signal of Uranine at various concentrations of quat and quat-neutralizer (QK-1000). The fluorescence signal of PTSA is reduced when the cationic quat is added, but the fluorescence signal of the uranine component is unchanged. When the quat-neutralizer is added, the quat-neutralizer binds tightly to the quat, and "frees" up the PTSA and its fluorescence signal is restored. As shown in FIG. 4B, there is a decrease in the PTSA fluorescence with added quat (the quantity is shown along the X-axis) while the uranine signal is unchanged. The PTSA fluorescence decreased up to a total of 10 ppm of active quat. The PTSA fluorescence returns with the addition of the QK1000 product and a total of 35 ppm of QK1000 was added to bring the PTSA fluorescence back to its original point.

Disclosed methods and systems of other embodiments may include an infusion device configured to apply a first amount of the cationic organic water treatment additive to the water stream, a measurement device configured to measure an amount of the active form of the cationic organic water treatment additive in the water stream, a monitor configured to monitor an output from the measurement device and a controller configured to adjust a second amount of the cationic organic water treatment additive applied to the water stream based on the amount of the active form of the cationic organic water treatment additive in the water stream.

Figure 5:
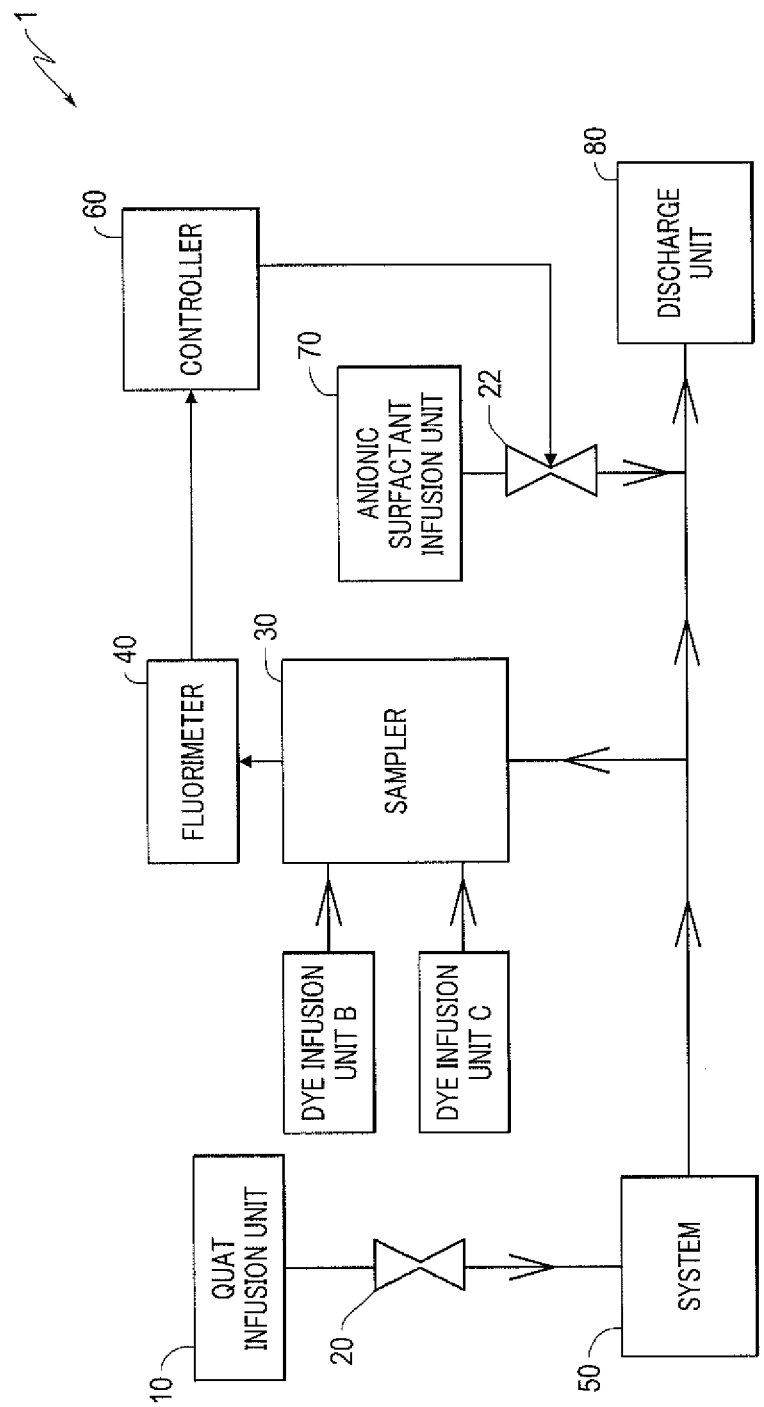
FIG. 5 is a schematic diagram of a control system for controlling quat concentration in a water system according to an embodiment.

The methods and techniques described herein can be incorporated in a variety of in-line or off-line automated control systems that may be adapted for a wide range of industrial water systems. Control systems may be used, for example, to ensure that any discharged water has been treated to a degree sufficient to neutralize residual cationic organic water treatment additive. An example of such a control system 1 is illustrated in FIG. 5 in which a sample containing a quantity of active quat is infused by infusion unit 10 via valve 20 into system 50. In sampler 30, a sample is pulled from an outflow of the system 50 and prepared by the addition of known concentrations of both a reactive dye via dye infusion unit B and a non-reactive dye via dye infusion unit C. The final prepared sample in sampler 30 is then evaluated by fluorimeter 40 to obtain a representative fluorescence signal ratio representing a ratio of the signal of the reactive dye to the signal of the non-reactive dye. The fluorimeter 40 may be any suitable fluorimeter known in the art. This ratio is then used by the controller 60 to compare to a baseline signal ratio of the reactive dye to the non-reactive dye at system initiation or at the initiation of any infusion interval thereafter to determine the concentration of active quat in the sample and the volume of anionic surfactant that needs to be added via anionic surfactant infusion unit 70 and valve 22 to neutralize the detected quat before the aqueous stream is suitable for discharge by discharge unit 80. The controller 60 may be a CPU and/or program executable on a CPU, or any controller known in the art.

Figure 6:
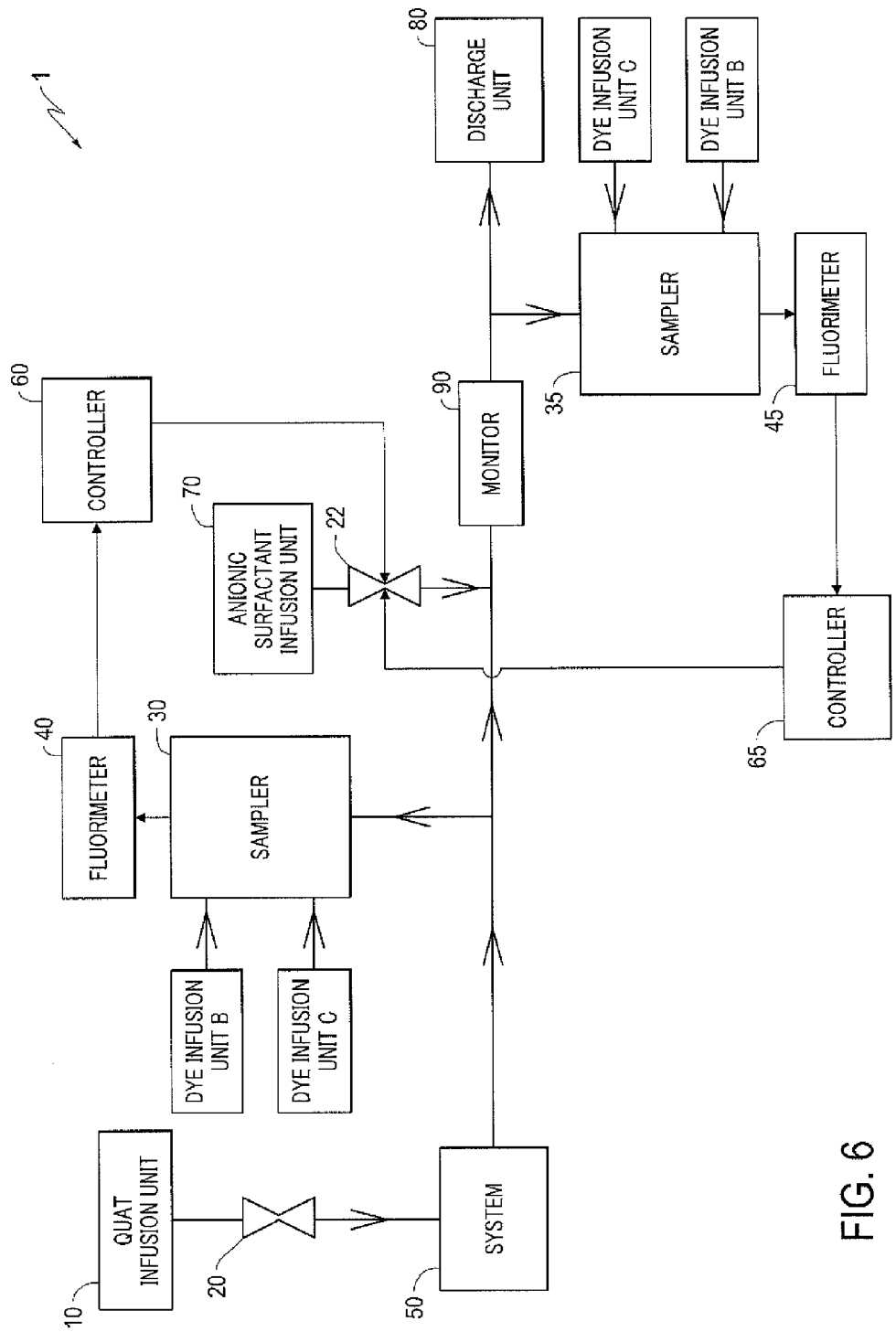
FIG. 6 is a schematic diagram of a control system for controlling quat concentration in a water system including monitoring the system after treatment with an anionic surfactant according to an embodiment.

FIG. 6 illustrates a modified version of the control system 1 illustrated in FIG. 5. In this embodiment, the system 1 can also monitor via monitor 90 the stream after treatment with the anionic surfactant to confirm successful suppression of the active quat and, if desired, be used for controlling or fine tuning the addition of the anionic surfactant. For example, known concentrations of reactive dye and non-reactive dye are added to the prepared sample in sampler 35 drawn from the stream after treatment with the anionic surfactant. The prepared sample is evaluated in a fluorimeter 40 to obtain a representative fluorescence signal ratio. This ratio is then used by the controller 65 to determine the concentration of active quat in the sample and the volume of any additional anionic surfactant that needs to be added to neutralize the detected quat before the aqueous stream is suitable for discharge by discharge unit 80.

Figure 7:
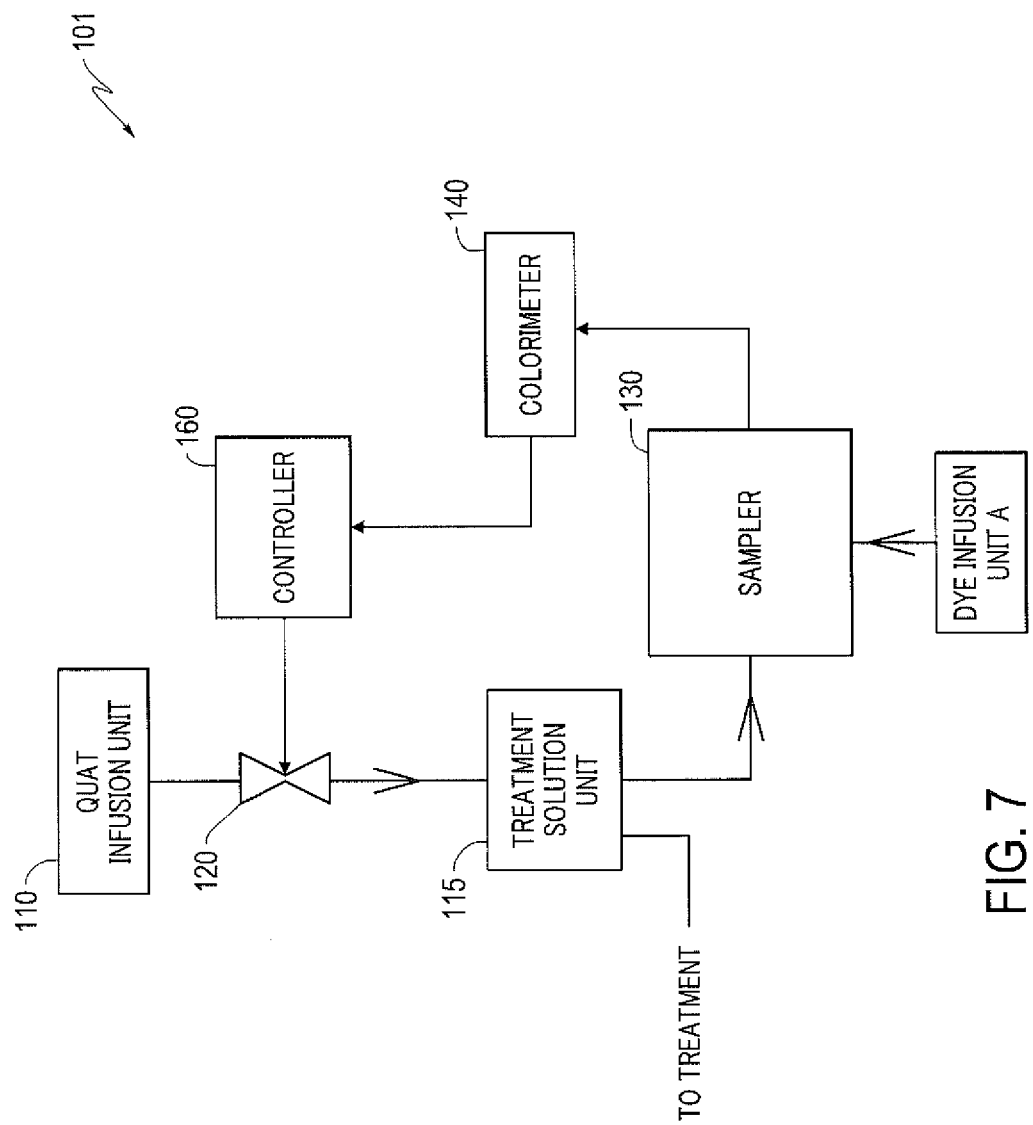
FIG. 7 is a schematic diagram of a control system for controlling the delivery of quat to a water system based on absorbance of a sample from the system according to an embodiment.

In another embodiment, a control system may be used in connection with the embodiment that applies to water an anionic dye with a relatively high affinity for the active form of the cationic organic water treatment additive and a relatively low affinity for the inactive form of the cationic organic water treatment additive and then measures a parameter of the water. The control system ensures that the cationic organic water treatment additive level of a treatment solution or working solution is sufficient to achieve its goal, e.g., the desired level of decontamination and/or disinfection in the case of cationic biocides. An example of such a control system 101 is illustrated in FIG. 7 in which a sample prepared in sampler 130 is pulled from the treatment solution unit 115. The sample is prepared via filtering and/or other processes disclosed herein to improve clarity and a suitable dye is added via dye infusion unit A. The prepared sample is then evaluated in a colorimeter 140 with the absorbance data being used by the controller 160 for adjusting the volume of quat 110 being added to the treatment solution in the treatment solution unit 115 via valve 120 for use in an industrial application.

Figure 8:
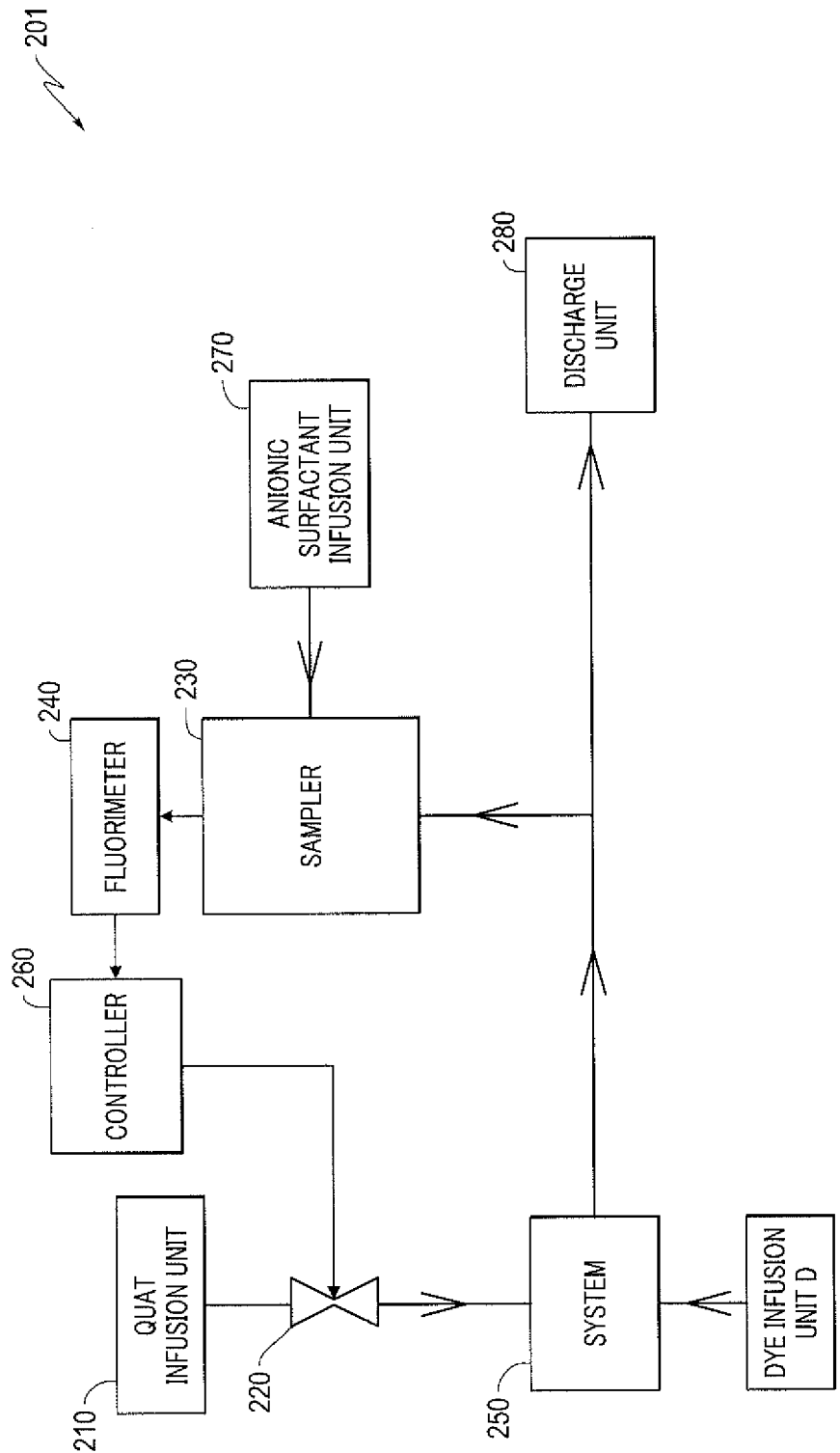
FIG. 8 is a schematic diagram of a control system for controlling the quat concentration in a water system according to an embodiment.

In other embodiments, control systems, such as control system 201 illustrated in FIG. 8 may be configured and operated in accord with the methods detailed herein. In particular, a fluorescent dye is added to the system 250 via a dye infusion unit D that is modified through addition of a suitable anionic surfactant 270 to the sample preparation in sampler 230. The fluorescence signal can be quantified by the fluorimeter 240. Data from the fluorimeter 240 can then be used for controlling via controller 260 the quat feed rate of the quat infused through quat infusion unit 210 via valve 220 to ensure that the target concentration range is being maintained within the system 250 and/or control the addition of additional quantities of anionic surfactant to ensure that substantially no active quat is discharged from the system 250 via discharge unit 280.

Figure 9:
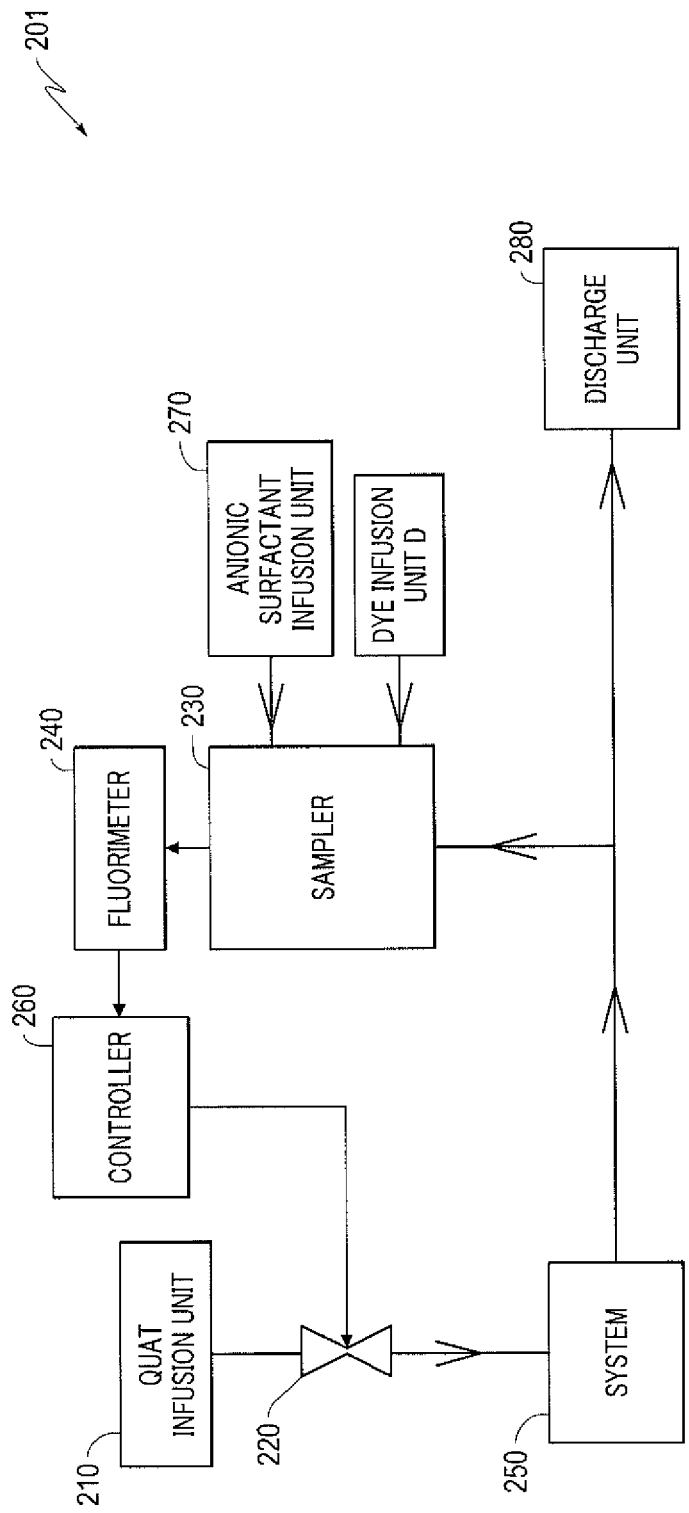
FIG. 9 is a schematic diagram of a control system for controlling the quat concentration according to an embodiment.
Figure 10:
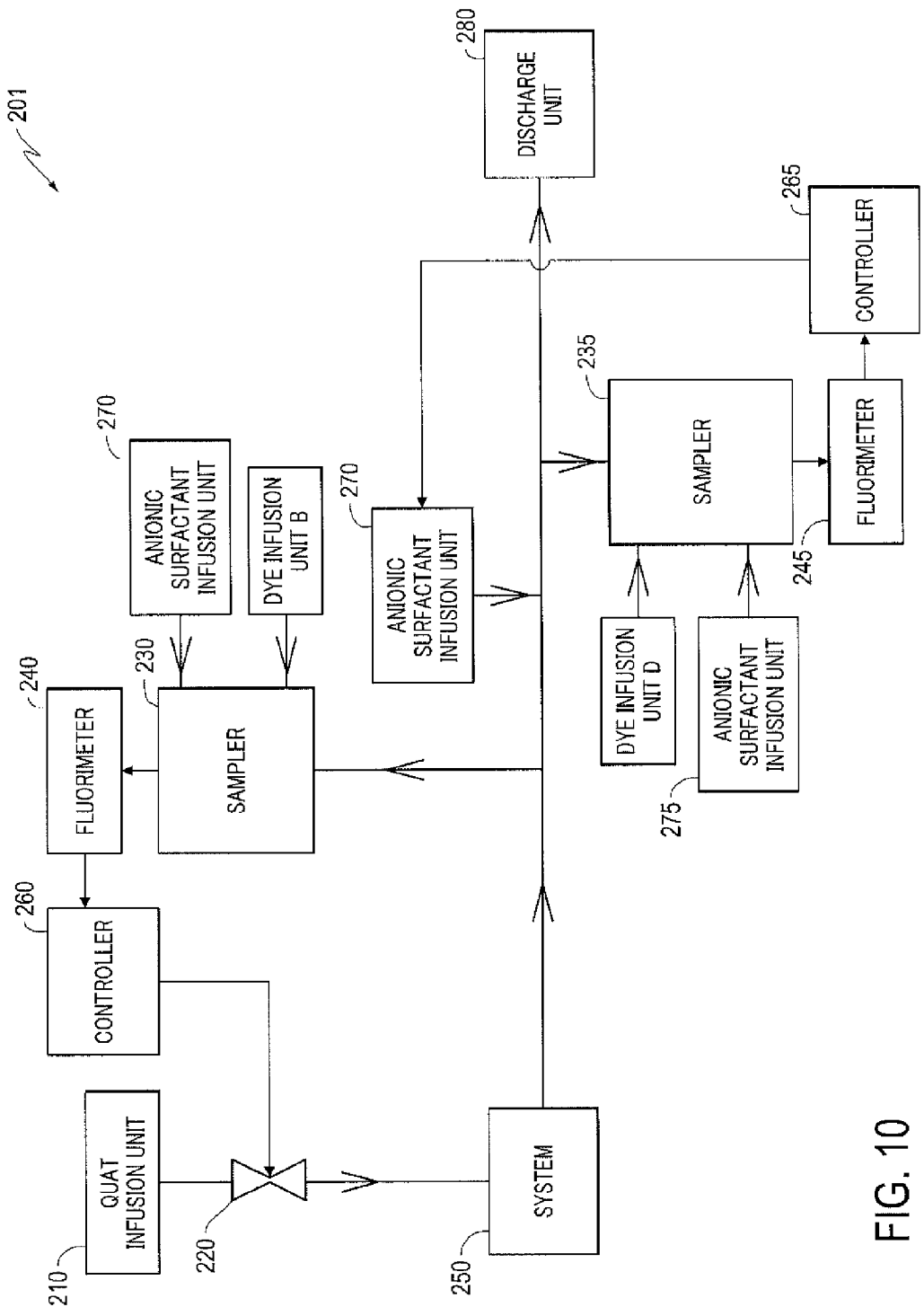
FIG. 10 is a schematic diagram of a control system for controlling the quat concentration according to an embodiment.

The embodiment of FIG. 9 differs from the embodiment of FIG. 8 only in that fluorescent dye is added via dye infusion unit D directly to the sample preparation in sampler 230 along with the anionic surfactant via anionic surfactant infusion unit 270. The embodiment of FIG. 10 differs from the embodiment of FIG. 9 in that, like the embodiment of FIG. 6, the embodiment of FIG. 10 includes a controller 265 and fluorimeter 245 that can be used for controlling or fine tuning the addition of the anionic surfactant to the sample preparation along with the fluorescent dye before discharge through the discharge unit 280.

Modifications of the basic control systems illustrated in FIGS. 5-10 may be made to provide additional monitoring locations and to adapt the control systems to the requirements of any particular industrial water system. Similarly, a combination of the techniques and methods detailed above may be combined in a single industrial water system to monitor and control various aspects of the system operations including, for example, that the concentration of cationic organic water treatment additive is sufficient, that the concentration of cationic organic water treatment additive does not exceed a target range, that the concentration of cationic organic water treatment additive is not excessive and/or that the efforts to remediate any residual cationic organic water treatment additive is efficient and effective. It is also contemplated that disclosed systems and methods be applied in in-line or off-line water systems.

It will be appreciated that the above-disclosed features and functions, or alternatives thereof, may be desirably combined into different systems or methods. Also, various alternatives, modifications, variations or improvements may be subsequently made by those skilled in the art, and are also intended to be encompassed by the following claims. As such, various changes may be made without departing from the spirit and scope of this disclosure as defined in the claims.

What is claimed is:

1. A method for controlling an amount of an anionic surfactant added to water in an industrial water system that includes a cationic organic water treatment additive, the method comprising:
   adding to the water (i) a first fluorescent dye configured to interact with the cationic additive thereby reducing a fluorescence intensity signal of the first fluorescent dye, and (ii) a second fluorescent dye that is substantially inert to the cationic additive, the first fluorescent dye and the second fluorescent dye being applied to the water in a predetermined concentration ratio;
   adding to the water an anionic surfactant that binds with the cationic additive thereby blocking the interaction of the first fluorescent dye with the cationic additive, which increases the fluorescence intensity signal of the first fluorescent dye;
   measuring a fluorescence intensity of each of the first fluorescent dye and the second fluorescent dye to establish a fluorescence intensity signal ratio;
   comparing the fluorescence intensity signal ratio to a predetermined fluorescence intensity signal ratio; and
   controlling an amount of the anionic surfactant added to the water based on the comparison of the fluorescence intensity signal ratio to the predetermined fluorescence intensity signal ratio.

2. The method according to claim 1, further comprising determining the amount of the anionic surfactant in the water based on the fluorescence intensity signal ratio.

3. The method according to claim 1, wherein the first fluorescent dye has a first fluorescence spectrum in the absence of cationic additive and has a second fluorescence spectrum when it interacts with the cationic additive.

4. The method according to claim 1, wherein the second fluorescent dye has a fluorescence spectrum in the absence of the cationic additive that is substantially unchanged in the presence of the cationic additive.

5. The method according to claim 1, wherein the fluorescence intensity signals are measured using a fluorimeter.

6. The method according to claim 1, wherein the first fluorescent dye is PTSA.

7. The method according to claim 1, wherein the second fluorescent dye is uranine.

8. The method according to claim 1, wherein the cationic additive is at least one of a cationic biocide, a cationic surfactant, and a cationic polymer.

9. The method according to claim 1, wherein the cationic additive is a cationic biocide.

10. The method according to claim 1, wherein the cationic additive is a quaternary amine compound.

11. The method according to claim 1, wherein the first fluorescent dye substantially interacts with an active form of the cationic additive.

12. The method according to claim 1, wherein the second fluorescent dye substantially does not interact with an active form of the cationic additive.

13. The method according to claim 1, wherein the water includes waste water in at least one of a food industry plant, a surface water system and a waste treatment plant.

14. The method according to claim 1, further comprising:
determining an amount of the cationic additive in the water based on the fluorescence intensity signal ratio by providing a standard curve relating the fluorescence intensity signal ratio to amounts of the cationic additive, the standard curve showing an expected response of the fluorescence intensity signal ratio based on changes in concentration of the cationic additive; and
comparing the first fluorescence intensity signal ratio to the standard curve.

15. The method according to claim 14, further comprising adding the cationic additive to the water at least until the expected response of the fluorescence parameter is observed, and determining a demand of the water for the cationic additive based on the added amount of cationic additive.

16. The method according to claim 15, further comprising controlling the amount of the cationic additive that is added to the water based on the determined demand.

17. The method according to claim 16, wherein the determined demand is a demand for an amount of active, unreacted cationic additive in the water.

18. The method according to claim 16, wherein the water is in an effluent stream of the industrial water system.

19. The method according to claim 16, wherein the water includes waste water in at least one of a food industry plant, a surface water system and a waste treatment plant.

20. The method according to claim 15, wherein the demand of the water is a demand for an amount of residual, unreacted forms of the cationic additive in the water.

21. The method according to claim 15, wherein the cationic additive is a quat-based disinfectant.

22. The method according to claim 21, further comprising controlling an amount of the quat-based disinfectant present in a waste stream of the industrial water system based on the determined demand thereby preventing excessive concentration of the quat-based disinfectant in the waste stream that would kill microbes used in downstream waste treatment plants.

23. The method according to claim 1, wherein the anionic surfactant is a laureth sulfate compound configured to neutralize an active form of the cationic additive.

24. The method according to claim 1, wherein a sufficient amount of the anionic surfactant is added to the water so that the second fluorescence intensity signal ratio substantially equals the first fluorescence intensity signal ratio.

25. The method according to claim 1, wherein the water has a level of turbidity that interferes with measuring the fluorescence intensity signals.

26. The method according to claim 1, wherein a dye infusion unit adds the first fluorescent dye and the second fluorescent dye to the water together.

27. The method according to claim 1, wherein the predetermined fluorescence intensity signal ratio is a ratio of a fluorescence intensity of each of the first fluorescent dye and the second fluorescent dye in water that includes a known amount of cationic additive.

28. The method according to claim 1, wherein a sufficient amount of aniconic surfactant is added so that the fluorescence intensity signal ratio corresponds to the predetermined fluorescence intensity signal ratio.

* * * * *